(12) United States Patent
Colwell, Jr. et al.

(10) Patent No.: US 11,540,895 B2
(45) Date of Patent: *Jan. 3, 2023

(54) APPARATUS AND METHODS FOR BALANCING A JOINT

(71) Applicant: Scripps Health, San Diego, CA (US)

(72) Inventors: Clifford W. Colwell, Jr., La Jolla, CA (US); Darryl David D'Lima, San Diego, CA (US)

(73) Assignee: Scripps Health, San Diego, CA (US)

( * ) Notice: Subject to any disclaimer, the term of this patent is extended or adjusted under 35 U.S.C. 154(b) by 545 days.

This patent is subject to a terminal disclaimer.

(21) Appl. No.: 16/456,270

(22) Filed: Jun. 28, 2019

(65) Prior Publication Data

US 2019/0388174 A1    Dec. 26, 2019

Related U.S. Application Data

(60) Continuation of application No. 15/056,855, filed on Feb. 29, 2016, now Pat. No. 10,376,332, which is a
(Continued)

(51) Int. Cl.
*A61F 2/46* (2006.01)
*A61B 90/00* (2016.01)
(Continued)

(52) U.S. Cl.
CPC .............. *A61B 90/06* (2016.02); *A61B 5/103* (2013.01); *A61B 5/1036* (2013.01); *A61B 5/1076* (2013.01); *A61B 5/4528* (2013.01); *A61B 5/4585* (2013.01); *A61B 17/1664* (2013.01); *A61B 17/1671* (2013.01);
(Continued)

(58) Field of Classification Search
CPC . A61F 2/46; A61F 2/461; A61B 17/16; A61B 17/1664; A61B 17/1671; A61B 17/1682; A61B 17/1684; A61B 17/1686; A61B 34/20; A61B 34/45; A61B 34/4585;
(Continued)

(56) References Cited

U.S. PATENT DOCUMENTS 5,733,292 A    3/1998   Gustilo et al.
7,442,196 B2   10/2008  Fisher et al.
(Continued)

OTHER PUBLICATIONS

International Search Report and Written Opinion dated Feb. 25, 2013 for corresponding Application No. PCT/US2012/54618.
(Continued)

*Primary Examiner* — Christopher J Beccia
(74) *Attorney, Agent, or Firm* — Knobbe, Martens, Olson & Bear, LLP

(57) ABSTRACT

A joint replacement balancing system which provides real-time feedback to a surgeon during a joint replacement surgery to assist the surgeon to balance a joint replacement. The joint replacement balancing system includes a non-transitory processor-readable medium storing code representing instructions to cause a processor to receive a signal from a joint balancing apparatus, determine if the joint replacement is out of balance, determine a corrective course of action to bring the joint into balance and generate and display to the surgeon during the joint replacement surgery a recommended corrective course of action to complete the joint replacement surgery.

13 Claims, 9 Drawing Sheets

Related U.S. Application Data division of application No. 13/230,583, filed on Sep. 12, 2011, now Pat. No. 9,307,929.

(51) Int. Cl.

| | | |
|---|---|---|
| *A61B 5/103* | (2006.01) | |
| *A61B 5/107* | (2006.01) | |
| *A61B 5/00* | (2006.01) | |
| *A61B 34/20* | (2016.01) | |
| *A61B 34/00* | (2016.01) | |
| *A61B 17/16* | (2006.01) | |
| *A61F 2/38* | (2006.01) | |

(52) U.S. Cl.
CPC ...... *A61B 17/1675* (2013.01); *A61B 17/1682* (2013.01); *A61B 17/1684* (2013.01); *A61B 17/1686* (2013.01); *A61B 34/20* (2016.02); *A61B 34/25* (2016.02); *A61F 2/461* (2013.01); *A61F 2/4657* (2013.01); *A61B 2034/252* (2016.02); *A61B 2034/254* (2016.02); *A61B 2090/064* (2016.02); *A61B 2090/065* (2016.02); *A61B 2090/067* (2016.02); *A61B 2562/04* (2013.01); *A61F 2/38* (2013.01); *A61F 2002/4666* (2013.01); *A61F 2002/4668* (2013.01); *A61F 2002/4688* (2013.01)

(58) Field of Classification Search
CPC ..... A61B 5/103; A61B 5/1036; A61B 5/1076; A61B 5/4528; A61B 5/4584
See application file for complete search history.

(56) References Cited

U.S. PATENT DOCUMENTS

| | | | | |
|---|---|---|---|---|
| 7,575,602 | B2 * | 8/2009 | Amirouche | A61B 5/076 623/18.11 |
| 7,578,821 | B2 | 8/2009 | Fisher et al. | |
| 7,615,055 | B2 | 11/2009 | DiSilvestro | |
| 7,632,283 | B2 | 12/2009 | Heldreth | |
| 7,708,740 | B1 | 5/2010 | Bonutti | |
| 7,837,691 | B2 * | 11/2010 | Cordes | A61F 2/4657 606/88 |
| 8,419,801 | B2 * | 4/2013 | DiSilvestro | A61F 2/389 623/23.45 |
| 9,307,929 | B2 * | 4/2016 | Colwell, Jr. | A61F 2/461 |
| 9,597,158 | B2 * | 3/2017 | Colwell, Jr. | A61B 17/1682 |
| 10,376,332 | B2 * | 8/2019 | Colwell, Jr. | A61B 5/4585 |
| 2004/0019382 | A1 | 1/2004 | Amirouche et al. | |
| 2004/0064191 | A1 | 4/2004 | Wasielewski | |
| 2005/0177169 | A1 | 8/2005 | Fisher et al. | |
| 2006/0009856 | A1 | 1/2006 | Sherman et al. | |
| 2007/0234819 | A1 | 10/2007 | Amirouche et al. | |
| 2009/0259319 | A1 * | 10/2009 | DiSilvestro | A61F 2/389 623/23.45 |
| 2010/0217156 | A1 | 8/2010 | Fisher et al. | |
| 2010/0249533 | A1 | 9/2010 | Pierce et al. | |
| 2010/0326194 | A1 | 12/2010 | Stein et al. | |
| 2010/0331633 | A1 | 12/2010 | Stein | |
| 2010/0331663 | A1 | 12/2010 | Stein | |
| 2010/0331733 | A1 | 12/2010 | Stein | |

OTHER PUBLICATIONS

U. Nolten, et al., "Sensor integrated tibial inlay for soft-tissue balancing," Procedia Chemistry 1 (2009) (4 pages).

"Optimum Flexion Gap and Ligament Balance," eLIBRA® Dynamic Knee Balancing System (4 pages).

"ELIBRA® Dynamic Knee Balancing System Surgical Technique and System Overview," Zimmer® Natural Knee II, Zimmer Personal Fit, Renewed Life.™ (25 pages).

"ELIBRA® Dynamic Knee Balancing System *Surgical Technique & System Overview*," Synvasive® Technology, Inc. (14 pages).

ELIBRA® "Dynamic Knee Balancing System Surgical Technique and System Overview," Zimmer® NexGen® Knee, Zimmer Personal Fit, Renewed Life.™ (26 pages).

"Reuse and reprocess of eLIBRA® Soft Tissue Force Sensor Devices," Synvasive Technology, Inc. (1 page).

Jian Wu, et al., "A method for dynamically measuring the Soft Tissue Balance in the Total Knee Replacement," IFMBE Proceedings, vol. 14/2 (5 pages).

Dennis, MD, "Measured Resection: An Outdated Technique in Total Knee Arthroplasty," Orthopaedic Crossfire® point, Orthopedics, Sep. 2008, retrieved from the Internet <URL:http://synvasive.com/resources/WP-Dennis-2011.pdf>.

Nevins, MD, et al., "Balancing the Perfect Knee, Case Report, Podium Presentation," ISTA, 2009, retrieved from the Internet <URL:http://synvasive.com/resources/eLIBRA-WP-Nevins-2010.pdf>.

Kreuzer, MD, et al., "Soft Tissue Balance in Primary Total Knee Arthroplasties Using a Force Sensing Device," Case Report, Podium Presentation, ISTA, 2009, retrieved from the Internet <URL:http://synvasive.com/resources/eLIBRA-WP-Esska-2010.pdf>.

Fetto, MD, et al., "Electronic Measurement of Soft Tissue Balancing Reduces Lateral Releases in Total Knee Arthroplasty," Retrospective Study, Podium Presentation, ISTA, 2009, retrieved from the Internet <URL:http://synvasive.com/resources/eLIBRA-WP-Fetto-2010.pdf>.

Hadley, MD, et al., "Correction of Severe Valgus Deformity with Non-Constrained Total Knee Arthroplasty Design," Case Report, Synvasive® Technology, Inc., retrieved from the Internet <URL:http://synvasive.com/resources/eLIBRA-Whitepaper-Hadley-Fetto.pdf>.

http://synvasive.com/video.php?id=Dounchis_Final&w=640&h=480.

http://synvasive.com/video.php?id=Camarata_eLIBRA_Zimmer_x264&w=640&h=480.

http://synvasive.com/video.php?id=Kreuzer-TKA-using-eLIBRA_x264&w=640&h=480.

* cited by examiner

APPARATUS AND METHODS FOR BALANCING A JOINT

CROSS-REFERENCE TO RELATED APPLICATIONS

This application is a continuation application of U.S. patent application Ser. No. 15/056,855, filed on Feb. 29, 2016, which is a divisional of U.S. patent application Ser. No. 13/230,583, filed on Sep. 12, 2011, the entirety of this application is hereby incorporated by reference herein. Any and all applications for which a foreign or domestic priority claim is identified in the Application Data Sheet as filed with the present application are hereby also incorporated by reference under 37 CFR 1.57.

BACKGROUND

The embodiments described herein relate generally to apparatus and methods for balancing an artificial joint, and more particularly to apparatus and methods for providing real-time feedback during a procedure for balancing an artificial joint.

Traumatic, inflammatory, and degenerative disorders of joints can lead to severe pain and loss of mobility. One source of joint pain is related to the inflammation or degeneration of the cartilage and/or bone of a joint, such as for example, arthritis. Bony contact or grinding of degenerated joint components can play a role in some pain syndromes.

One current standard of care to address the degenerative problems with a joint is to replace all or part of the joint. By performing this surgical procedure, the contact or grinding of the degenerated joint can be stopped, thus stopping any potential pain generated as a result thereof. Performing this surgical procedure, however, may also change the range of motion of the replacement joint relative to both a healthy joint and the degenerated joint. Because of the change in the range of motion of the joint, the surgeon performing the joint replacement must balance the joint accurately during the initial procedure to both maximize the range of motion of the joint, and to reduce the likelihood of follow up procedures. If not properly balanced, the replacement joint can be subject to, for example, excessive wear, instability and loosening.

Accordingly, a need exists for apparatus and methods to balance a joint during a joint replacement procedure.

DETAILED DESCRIPTION

Figure 1:
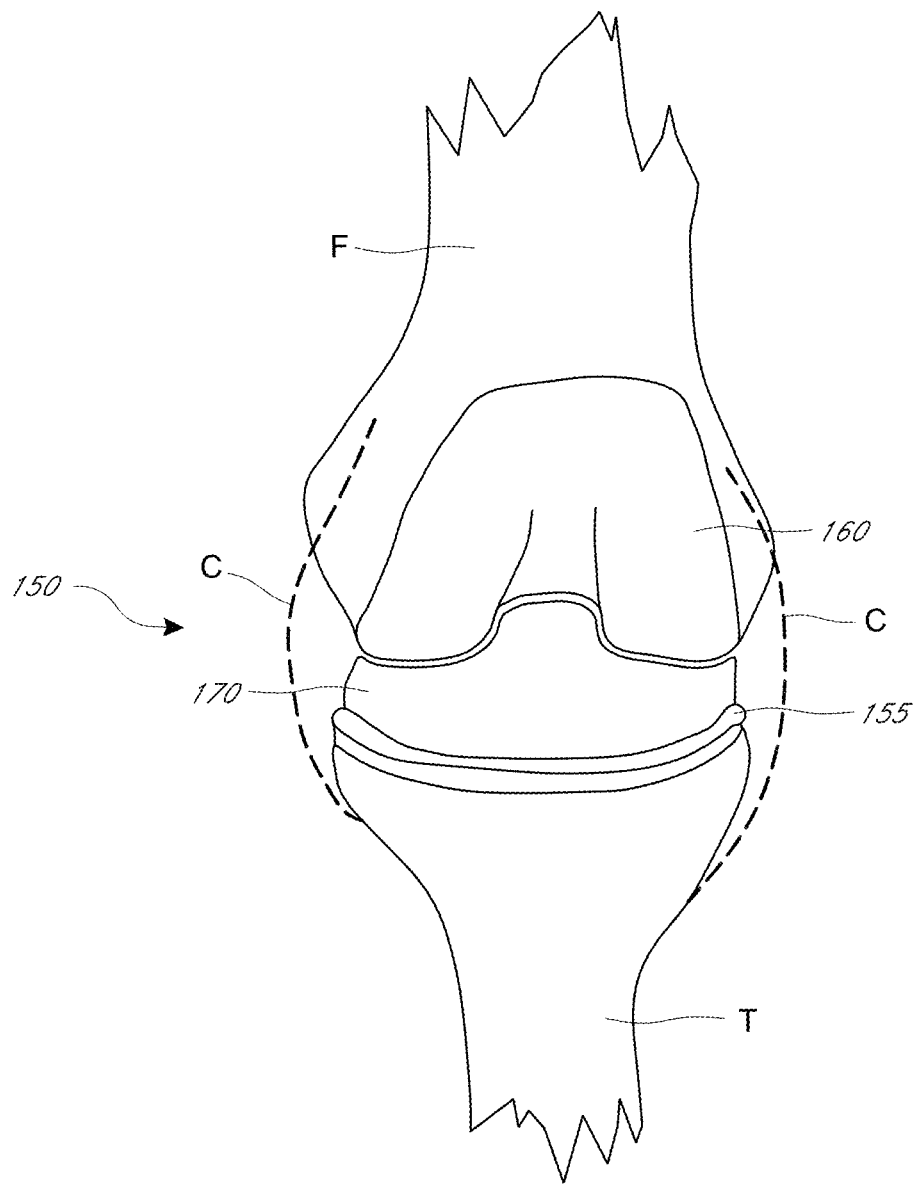
FIG. 1 is an illustration of a conventional joint replacement apparatus.

In some embodiments, an apparatus for balancing a joint includes a first portion configured to be coupled to a first bony structure and a second portion configured to be coupled between the first portion and a second bony structure. The second bony structure is disposed opposite the first bony structure. The apparatus further includes a transducer and/or an actuator coupled between the first portion and the second portion. In some embodiments, the transducer is used to convert various inputs/readings (e.g., force, pressure, rotation) to output signals associated with the apparatus. In some embodiments, the transducers can be associated with actuators to respond to external signals and cause movement of the apparatus 2 as described herein. In some embodiments, the apparatus can have separate transducers and actuators or the transducers and actuators can be part of the same component. In some embodiments, the transducer/actuator is a piezoelectric material, which can be configured as both a sensor/transducer and an actuator.

In some embodiments, a method for balancing a joint includes outputting a signal including a first data set associated with at least one of a force, a position, a displacement or a rotation associated with an apparatus. The apparatus is disposed between a first bony structure and a second bony structure, and includes a first portion configured to be coupled to the first bony structure, a second portion configured to be disposed between the first portion and the second bony structure, and a transducer and/or an actuator disposed between the first portion and the second portion.

The method for balancing a joint further includes outputting a signal including a second data set, the second data set associated with at least one of a force, a position, a displacement or a rotation associated with the apparatus after the performance of at least a part of a surgical procedure. The surgical procedure is based at least in part on a recommendation based on the first data set. The method further includes moving, in response to the received signal, a movable portion of the transducer and/or actuator (or one or both of the first portion or the second portion of the apparatus). The movable portion of the actuator causes one of the first and second portion of the apparatus to move with respect to the other of the first and second portion of the apparatus.

In some embodiments, a non-transitory processor-readable medium stores code representing instructions to cause a processor to receive a signal including a first data set associated with at least one of a force, a position, a displacement or a rotation associated with an apparatus. The apparatus is disposed between a first bony structure and a second bony structure, and includes a first portion configured to be coupled to the first bony structure, a second portion configured to be disposed between the first portion and the second bony structure, and a transducer and/or an actuator disposed between the first portion and the second portion. The non-transitory processor-readable medium further stores code representing instructions to cause a processor to generate, based on the first data set, a recommended action to complete a surgical procedure, the generating occurring during the surgical procedure.

As used in this specification, the term "joint" includes any joint or location at which two or more bones are in close proximity, such as for example, a knee joint, a shoulder joint, a hip joint, a spine or portion of a spine, an elbow joint, an ankle, and/or a patellofemoral joint. As used in this specification, the term "bony structure" can include any bone, bone portion, and/or other bony structure associated with a joint, such as for example, a portion of a tibia, a portion of a femur, a portion of a humerus, a portion of a scapula, a portion of a pelvis, a portion of a vertebra, a portion of an ulna, or a portion of a talus. While a total joint arthroplasty is generally shown and described, unicompartmental and/or partial joint replacement is also contemplated.

As used in this specification, the words "proximal" and "distal" refer to a location closer to and away from, respectively, a torso and/or another location central to a body. Thus, for example, the end of a femur closer to the knee joint would be the distal end of the femur, while the end of the femur closer to the hip joint would be the proximal end of the femur.

As used in this specification, the singular forms "a," "an" and "the" include plural referents unless the context clearly dictates otherwise. Thus, for example, the term "a transducer" is intended to encompass a single transducer or multiple transducers.

Conventional knee arthroplasty (i.e., joint replacement) involves replacement of some or all of the knee joint. FIG. 1 illustrates an artificial knee joint 150 including a tibial portion 155 coupled to a proximal end of a tibia T and a femoral portion 160 coupled to a distal portion of a femur F. An interface or contact portion 170 is disposed between the tibial portion 155 and the femoral portion 160. The interface portion 170 has a surface configured to slidingly nest with the outer surface of the femoral portion 160 such that the knee joint is able to rotate through its natural range of motion. Connective tissue C (represented by dashed lines) maintains the femur F and tibia T in the appropriate relative position.

Figure 2:
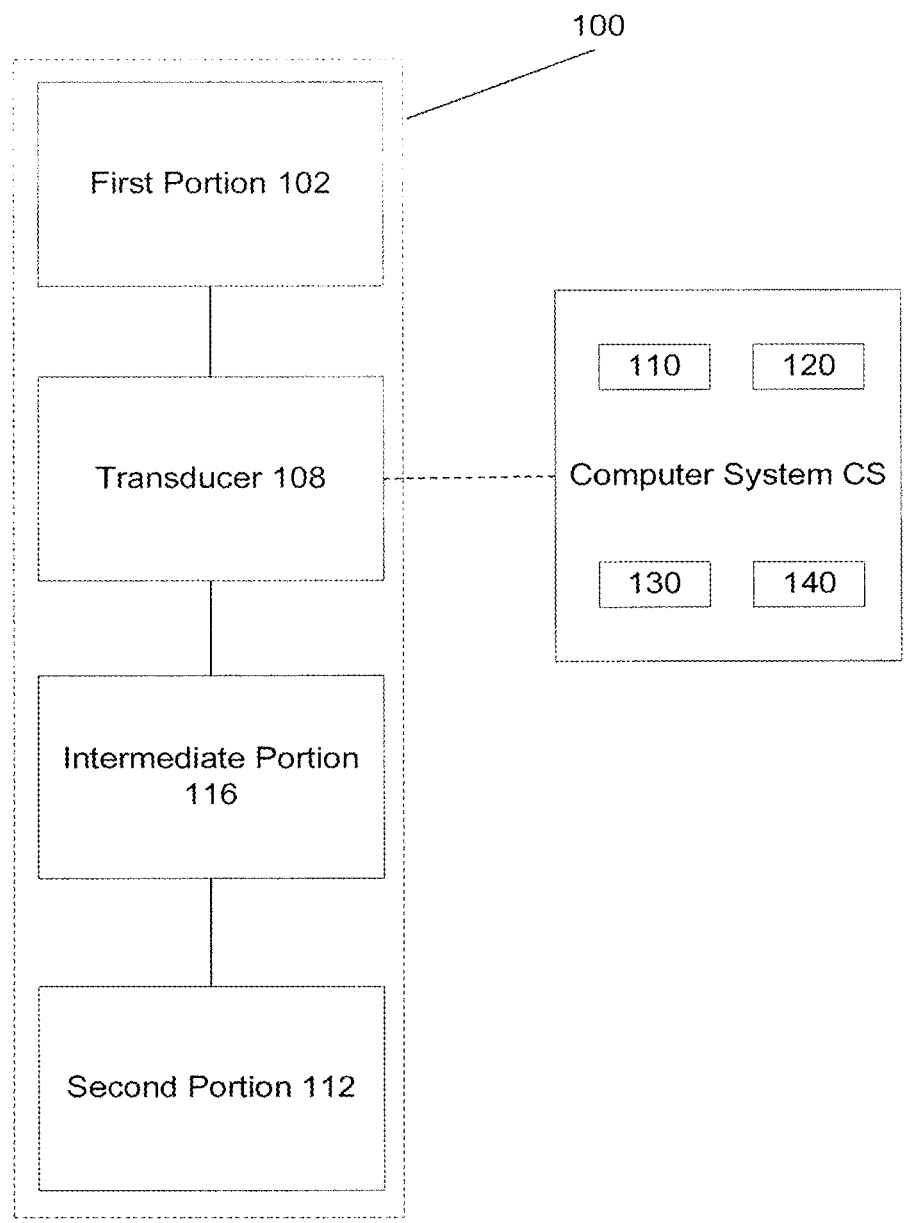
FIG. 2 is a functional block diagram of a joint balancing apparatus according to an embodiment.

FIG. 2 is a functional block diagram of a joint balancing apparatus 100. Joint balancing apparatus 100 can be a temporary, permanent, or semi-permanent implant configured to replace a joint and/or to provide data used to provide real-time feedback to a surgeon. The real-time feedback can be used by the surgeon to properly balance the joint during the surgical procedure. Real-time feedback can include recommended actions for completing a surgical procedure, such as for example, to make a specific bone cut and/or 4 loosen or tighten one or more connective tissues associated with the joint. After the joint is balanced, joint balancing apparatus 100 can be either completely or partially replaced by a permanent replacement joint. In other words, either the entirety of joint balancing apparatus 100 or a portion of joint balancing apparatus 100 can be replaced, or joint balancing apparatus 100 can remain in place and can function as the permanent replacement joint. Alternatively, an appropriate prosthesis/device that corrects the imbalance can be selected for implantation. Joint balancing apparatus 100 includes a first portion 102, a second portion 112, a transducer 108, and an intermediate portion 116. Transducer 108 can be operatively coupled to a computer system CS. In some embodiments, joint balancing apparatus 100 includes a separate actuator (not illustrated), operatively coupled to the computer system CS.

First portion 102 is configured to be coupled to a first bony structure (not shown in FIG. 2), such as a proximal portion of a tibia. In some embodiments, first portion 102 can be coupled to the first bony structure substantially flush with the first bony structure. In such embodiments, first portion 102 can be held in place by a temporary or permanent adhesive, and/or another temporary or permanent fastener. In other embodiments, first portion 102 can include a mount (not shown in FIG. 2) configured to extend from first portion 102 and into the first bony structure. In such embodiments, the mount can be shaped to correspond to a cavity formed in the first bony structure. In some embodiments including the mount, the mount can be held in place by a temporary or permanent adhesive, by friction within the cavity, and/or by another temporary or permanent fastener. In some embodiments, the mount can be permanently coupled to, and/or monolithically formed with, first portion 102. In other embodiments, the mount can be removably coupled to first portion 102. In these embodiments, the mount can be a first mount, and the first mount can be used during a balancing procedure on a joint, and the first mount can be replaced by a second mount, during and/or after the balancing procedure, the second mount configured to remain in the joint after the balancing procedure.

Second portion 112 is configured to be coupled between the first portion and a second bony structure (not shown in FIG. 2) such as a distal portion of a femur. In some embodiments, second portion 112 can be slidably coupled to the second bony structure. For example, second portion 112 can move relative to the second bony structure and can maintain a point of contact with the second bony structure, and the point of contact between the second bony structure and second portion 112 can change as the first bony structure moves relative 5 to the second bony structure. In some embodiments, the second bony structure can be in direct contact with second portion 112. In other of these embodiments, a contact portion (not shown in FIG. 2) can be disposed between the second bony structure and second portion 112. In such embodiments, the contact portion can be fixedly coupled to the second bony structure or the second portion 112, and the contact portion can be slidably coupled to the other of the bony structure or the second portion 112.

Intermediate portion 116 is configured to be disposed between first portion 102 and second portion 112 and can be configured to restrict, limit, or otherwise define, the movement of first portion 102 relative to second portion 112. Said another way, intermediate portion 116 can define the ranges of motion of first portion 102 relative to second portion 112. In some embodiments, the intermediate portion 116 can be one of a post, a bearing, or a gasket. In some embodiments, intermediate portion 116 can define an area between first portion 102 and second portion 112, the area configured to include transducer/actuator 108.

Knee balancing apparatus 100 can include transducer 108 configured to output data associated with knee balancing apparatus 100 and its interaction with the joint in which it is positioned. Transducer 108 can be disposed between first portion 102 and second portion 112. In some embodiments, transducer 108 can be disposed in an area between first portion 102 and second portion 112 defined by intermediate portion 116. In some embodiments, transducer 108 can include a fixed portion coupled to one of first portion 102 or second portion 112, and can include a movable portion coupled to the other of first portion 102 or second portion 112. In such embodiments, the movable portion of transducer 108 can be movable relative to the fixed portion of transducer 108 and functions as an actuator (i.e., causes relative movement of first portion 102 and second portion 112. In some embodiments, the fixed portion of transducer/actuator 108 can be fixedly coupled to one of first portion 102 and second portion 112. In some embodiments, the movable portion of transducer/actuator 108 can be slidably coupled to one of first portion 102 and second portion 112. In some embodiments, transducer/actuator 108 can be a plurality of transducers/actuators 108. In some embodiments, transducer/actuator 108 can be embedded in the intermediate portion 116. In some embodiments transducer 108 and actuator are arranged as a single component. In some embodiments, the transducer and the actuator are separate components.

Transducer 108 can be configured to record measurements and output data, such as for example, force data, position data, displacement data, and/or rotation data. 6 Specifically, transducer 108 is configured to output the data during a surgical procedure. In some embodiments, transducer 108 can output data regarding first portion 102 relative to second portion 112. By way of example, transducer 108 can be configured to output data, such as for example, a force generated between first portion 102 and second portion 112, a position or displacement of first portion 102 relative to second portion 112, and/or movement of first portion 102 relative to second portion 112 as the joint in which it is positioned rotates through a range of motion. In some embodiments, transducer 108 can output a plurality of data signals in absolute terms, as a function of time, and/or as a function of the distance traveled, e.g. range of motion of a joint. Said another way transducer 108 can output data at predetermined intervals, such as for example, every one second. In other embodiments, the interval can be longer or shorter. In other embodiments, transducer 108 can continuously output data.

Transducer 108 can be operatively coupled to and configured to output data to computer system CS. Computer System CS can be a known computer system that can include a processor 110, a memory 120, input/output devices, including an output module 130, and a communications module 140. The processor 110 can be a general-purpose processor or other processor configured to execute one or more instructions. In some embodiments, the processor 110 can alternatively be an application-specific integrated circuit (ASIC) or a field programmable gate array (FPGA). The memory 120 can be any fixed or removable memory, such as a Random Access Memory (RAM), Read Only Memory (ROM), a hard disk drive, a solid-state drive (SSD), an optical drive, a flash memory drive, other removable media. The output module 130 can be a hardware-based and/or software-based module (executing in hardware) configured to output data. For example, the output module 130 can be a hardware module (e.g., a graphics card) operatively coupled to a software module (e.g., a video driver). In the example, the output module 130 can be operatively and/or physically coupled to a visual display device, such as a monitor, television, projector, or other display screen or device. Alternatively, the output module 130 can be a hardware and/or software module configured to output an audio or tactile output representing data and/or media. In some embodiments, the output module 130 can be configured to output any combination of audio, video, graphical, or tactile feedback and/or output. More specifically, the output module 130 can be configured to output information associated with a recommended course of action for a surgical procedure based on the data received from the transducer 108. In some embodiments, the output module 130 can output the recommendations in response to one or more messages, data frames, data packets and/or other information received from the transducer. In some embodiments, the output module 130 can be configured to display any of the above-described information as a chart, graph, animation, or other graphical figure or resource. In some embodiments, the output can drive an actuator to cause movement of the portions of the knee balancing apparatus to which it is coupled.

For example, computer system CS can be configured to receive the data from transducer 108 and can generate a signal indicative of recommended action to balance the joint. Said another way, the signal can indicate to a surgeon to make a specific bone cut and/or loosen and/or tighten one or more connective tissues associated with the joint. In some embodiments, the actuator can receive the signal from the computer system and can move first portion 102 relative to second portion 112 to simulate the results of the recommended action.

Communication module 140 can be a hardware-based and/or software-based module (executing in hardware) configured to exchange information with one or more transducers. More specifically, the communication module 140 can include one or more network communication cards, drivers and/or other hardware and/or software modules configured to send information to and/or receive information from a network and/or one or more server or client devices. Thus, in some embodiments, the communication module 140 can communicate across a network with the transducer(s) 108 and actuators. In some embodiments, the computer system CS can be a centralized system in communication with the transducer(s) 108 and actuators and a remote graphical display (i.e., the display in the procedure room during the surgical procedure. In such embodiments, the computer system CS can be used to communicate with multiple transducers/actuators in separate procedure rooms either simultaneously or serially.

The network across which the computer system CS communicates can be any computer network configured to receive and send information between each or any of the peripheral device transducers 108, actuators, and the computer system CS. The network can include one or more computer devices, such as switching, routing, storage and/or other devices. In some embodiments, the network can be a local area network (LAN), wide area network (WAN), organization intranet, or the Internet.

FIGS. 3-6 depict examples of implementations of a joint balancing apparatus, specifically a knee balancing apparatus, and methods of balancing a knee joint using the knee balancing apparatus. While references made with respect to FIGS. 3-6 are directed to the knee joint, apparatus and methods having similar features can be equally applicable to other joints as discussed herein. Knee balancing apparatus 200 can be a temporary, permanent, or semi-permanent implant configured to replace at least a portion of a knee joint and to provide data used to provide real-time feedback to a surgeon during a surgical procedure. The feedback based on the data associated with the procedure can be used by the surgeon to properly balance the knee joint. After the knee joint is balanced, the knee balancing apparatus 200 can be replaced by a permanent replacement knee (e.g., as illustrated in FIG. 1). In some embodiments, only a portion of the knee balancing apparatus 200 is replaced with a permanent implant, or the entire knee balancing apparatus 200 can remain in place and can function as the permanent replacement knee joint.

Figure 3:
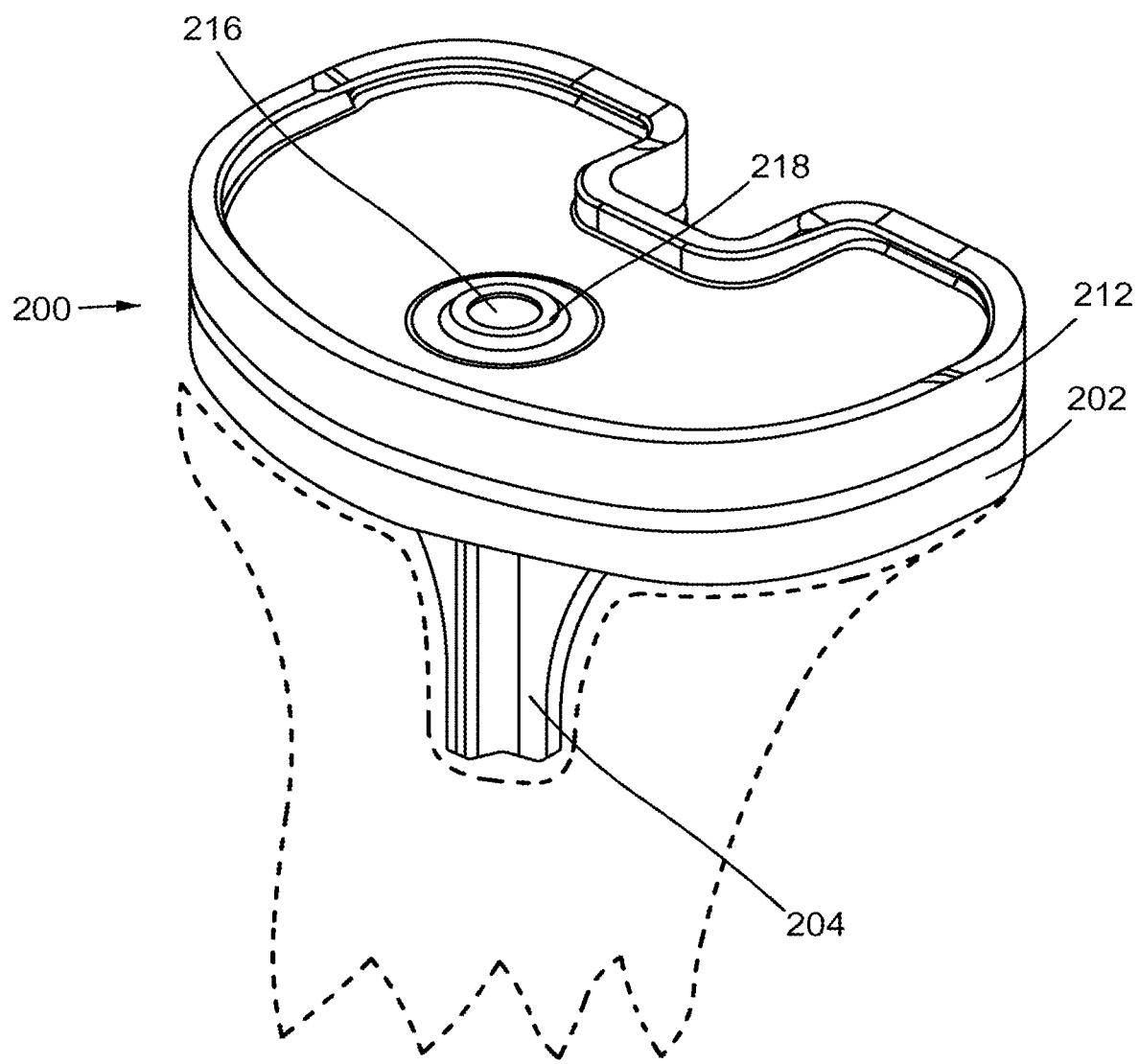
FIG. 3 is a perspective view of a joint balancing apparatus according to an embodiment.
Figure 4:
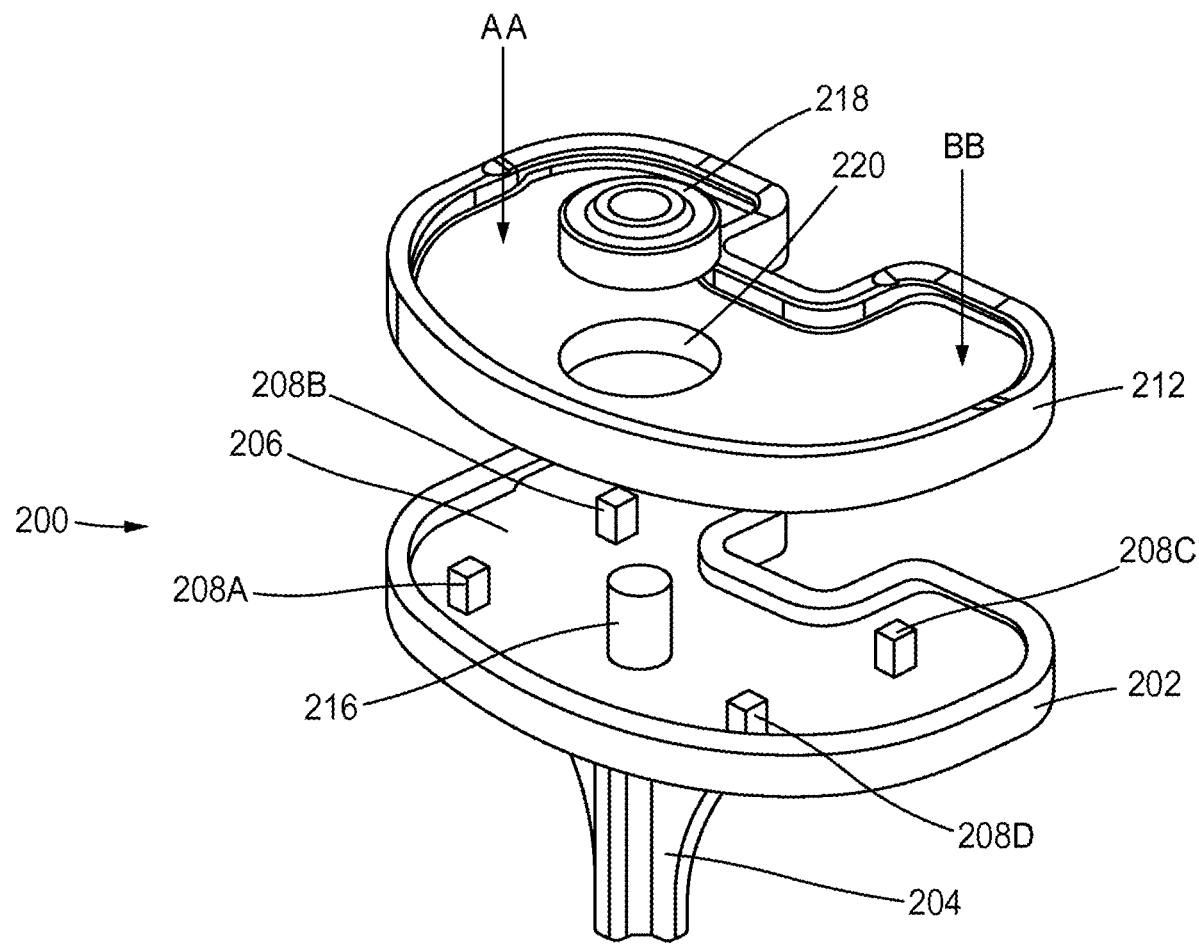
FIG. 4 is an exploded perspective view of the joint balancing apparatus shown in FIG. 3.

FIG. 3 is a perspective view of a knee balancing apparatus 200, and FIG. 4 is an exploded perspective view of knee balancing apparatus 200. As illustrated, knee balancing apparatus 200 substantially corresponds to/simulates the tibial portion 155 of implant 150 of FIG. 1. In other words, during a knee arthroplasty procedure, the knee balancing apparatus 200 is used to at least temporarily simulate the configuration and position of the tibial portion to ultimately be placed in the knee. Knee balancing apparatus 200 includes a first portion 202, a second portion 212, an intermediate portion 216, and four transducers and co-located actuators 208A, 208B, 208C, and 208D (collectively "transducers/actuators 208"). While depicted in FIG. 3 and FIG. 4 as including four transducers/actuators 208, in some embodiments, knee balancing apparatus 200 can include more or fewer transducers/actuators 208 or one or more arrays of transducers/actuators 208. In some embodiments, the apparatus includes only transducers 208 and need not include actuators.

First portion 202 is configured to be coupled to a proximal portion of a tibia (represented by dashed lines in FIG. 3). In some embodiments, first portion 202 can be coupled to the proximal portion of a tibia substantially flush with the proximal portion of the tibia. In such embodiments, first portion 202 can be held in place by a temporary or permanent adhesive, and/or another temporary or permanent fastener. First portion 202 includes a mount 204 configured to extend from first portion 202 and into the proximal portion of the tibia. Mount 204 can be shaped to correspond to a cavity formed in the 9 proximal portion of the tibia. The mount can be held in place by a temporary or permanent adhesive, by friction within the cavity, and/or by another temporary or permanent fastener. In some embodiments, the mount can be permanently coupled to, and/or monolithically formed with, first portion 202. In other embodiments, the mount can be removably coupled to first portion 202. In some embodiments, the mount can be a first mount, and the first mount can be used during a balancing procedure on a knee joint, and the first mount can be replaced by a second mount, during and/or after the balancing procedure. The second mount is configured to remain in the knee joint after the balancing procedure. First portion 202 includes a proximal surface 206. Proximal surface 206 is configured to be operatively coupled to transducers/actuators 208 and intermediate portion 216.

Second portion 212 is configured to be coupled between first portion 202 and a distal portion of a femur (not shown in FIGS. 3 and 4). In some embodiments, second portion 212 can be slidably coupled to the distal portion of the femur. For example, second portion 212 can move relative to the distal portion of the femur and can maintain a point of contact with the distal portion of the femur, and the point of contact between the distal portion of the femur and second portion 212 can change as the proximal portion of the tibia moves relative to the distal portion of the femur. In some embodiments, the distal portion of the femur can be in direct contact with second portion 212. In other embodiments, a contact or interface portion (not shown in FIGS. 3 and 4) can be disposed between the distal portion of the femur (or a femoral portion of an implant) and the second portion 212 (i.e., similar to the conventional configuration illustrated in FIG. 1). In such embodiments, the femoral portion can be fixedly coupled to the distal portion of the femur, and the contact or interface portion can be coupled to second portion 212. The contact portion of the second portion 212 can include a layer of material, such as polymeric material, configured to reduce friction between the contact portion and the femoral portion of the implant. In some embodiments, the shape of the second portion 212 is configured to conform to the shape of the permanent implant that will be put in place during the surgical procedure. In other words, the second portion can be configured to mimic the shape of the interface portion of the ultimate implant.

In some embodiments, second portion 212 defines an aperture 220 configured to receive a bearing 218 of intermediate portion 216. Second portion 212 can include a distal surface (not shown in FIGS. 3 and 4) configured to be operatively coupled to transducers 208.

Intermediate portion 216 and bearing 218 are disposed between first portion 202 and second portion 212. Intermediate portion 216 is fixedly coupled to first portion 202 and movably coupled to second portion 212. In this manner, intermediate portion 216 is configured to restrict, limit, or otherwise define, the movement of first portion 202 relative to second portion 212. Said another way, intermediate portion 216 defines the ranges of motion of second portion 212 relative to first portion 202. A portion of intermediate portion 216 is disposed within bearing 218 and within second portion 212. Bearing 218 allows intermediate portion 216 to have a greater or lesser range of motion within aperture 220 of second portion 212. In this manner, changing the characteristics of bearing 218 can increase or decrease the range of motion of intermediate portion 216 within aperture 220 of second portion 212, and subsequently can increase or decrease the range of motion of second portion 212 relative to first portion 202. In some embodiments, there are multiple intermediate portions 216. In other embodiments, there are no intermediate portions 216. In other embodiments, there is an intermediation portion formed by, or formed with transducer/actuator 208. In some embodiments, the intermediate portion 216 is instrumented to measure displacement and rotation, or can be actuated to control displacement and rotation similar to the manner described in connection with the transducers/actuators 208 herein.

Transducers/actuators 208 are configured to output data associated with knee balancing apparatus 200. Transducers/actuators 208 are disposed between first portion 202 and second portion 212. Transducers/actuators 208 can each include a fixed portion coupled to one of first portion 202 or second portion 212, and can each include a movable portion coupled to the other of first portion 202 or second portion 212. The movable portions of transducers/actuator 208 can be movable relative to the fixed portions of transducers/actuators 208. In some embodiments, the fixed portions of transducers/actuators 208 can be fixedly coupled to one of first portion 202 and second portion 212. In some embodiments, the movable portions of transducers/actuators 208 can be slidably coupled to one of first portion 202 and second portion 212. Examples of transducers suitable for use with the apparatus 200 include the NK Instrumented Tibial Plateau available from NK Biotechnical, Minneapolis, Minn. While transducers/actuators 208 are described as a single component, it should be understood that separate components may be utilized (i.e., physically distinct and separate components).

Transducers/actuators 208 are configured to output data during a surgical procedure, such as for example, force data (e.g., magnitude and direction), position data, displacement data, and/or data associated with the relative position of the first portion 202 with respect to the second portion 212 as the apparatus 200 rotates through a range of motion during a surgical procedure. In some embodiments, transducers/actuators 208 can output a plurality of data signals in absolute terms, as a function of time, and/or as a function of the distance traveled, e.g. range of motion of a joint. Said another way, transducers/actuators 208 can output data at predetermined intervals, such as for example, every one second. In other embodiments, the interval can be longer or shorter. In other embodiments, the transducers/actuators 108 can continuously output data as a procedure is performed and during movement of the tibia through its full range of motion. Each of transducers/actuators 208 can output different data based at least on the location of the transducer/actuator relative to each of the other transducers/actuators 208 and the forces imparted thereon. By way of example, if a force indicated in the location of arrow AA in FIG. 4 is greater than a force indicated in the location of arrow BB in FIG. 4, transducer/actuator 208A and transducer/actuator 208B will output force data indicating a first force or forces, and transducer/actuator 208C and transducer/actuator 208D will output force data indicating a second force or forces, less than the first force or forces.

Transducers/actuators 208 are configured to output data to a computer system (not shown in FIGS. 3 and 4) as discussed herein. The computer system can be configured to receive the data from transducers/actuators 208 and can generate a signal indicative of a recommended action to balance the knee joint. Said another way, the signal can indicate to a surgeon to make a specific bone cut and/or loosen one or more connective tissues associated with the knee joint.

In some embodiments, the first portion 202 and the second portion 212 are spaced parallel to one another at a known distance (e.g., 3-5 mm) and the forces are measured. As discussed in greater detail herein, based on the force information provided by the transducers and the predetermined distance between the first portion and the second portion, a recommended surgical procedure can be generated. With continued reference to the example above, the computer system can make a recommended action designed to reduce and/or increase the force AA and/or the force BB such that the force imparted between first portion 12 202 and second portion 212 is balanced (i.e., the same across the entire area between the two portions).

The computer system includes an algorithm, discussed in detail herein, designed to interpret the data received from the transducers in making a recommendation for a surgical procedure to correct any perceived imbalance. The algorithm is configured to account for the force data throughout a range of motion of the tibia. In some embodiments, a recommended surgical correction is not provided until the knee joint is moved through the range of motion. In some embodiments, the transducers 208 are configured to detect when the range of motion is complete. In other embodiments, a user can manually indicate when the transducers should start and stop measurement.

In some embodiments, the algorithm is configured to account for data relevant to the body of the person into which the implant is being placed. For example, the algorithm can be programmed to account for any one or more of several factors including body weight, height, gait cycle, leg height/length, bone malformations, soft tissue/muscle defects, neurological disorders, age, gender, activity level, etc.

In some embodiments, transducers/actuators 208 can receive a signal from the computer system and can be actuated to cause first portion 202 to move relative to second portion 212 to simulate the recommended corrective action. With continued reference to the example above, in some embodiments transducers/actuators 208 can receive the signal indicative of the recommended action from the computer system and the movable portions of one or more of transducer/actuator 208A, transducer/actuator 208B, transducer/actuator 208C, and/or transducer/actuator 208D, can move relative to the fixed portion of its respective transducer/actuators 208 to simulate the results of the recommended action. In other words, in a situation where the recommended surgical correction is to change the angle of, for example, a particular bone cut, the transducers can actuate to cause the second portion 212 to move to a position simulating that angle (e.g., shorten one or more transducers).

Figure 5:
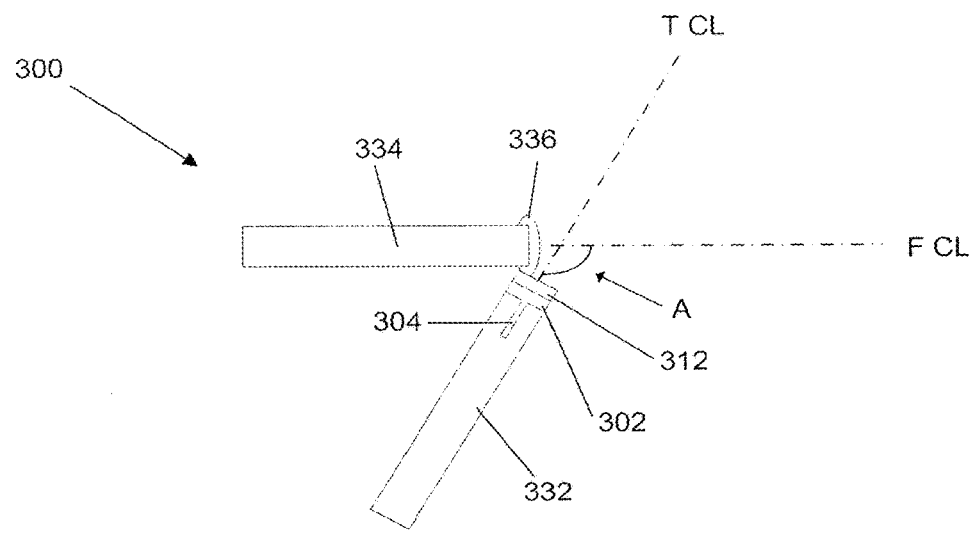
FIG. 5 is a schematic view of a joint and joint balancing apparatus according to an embodiment in a first configuration.
Figure 6:
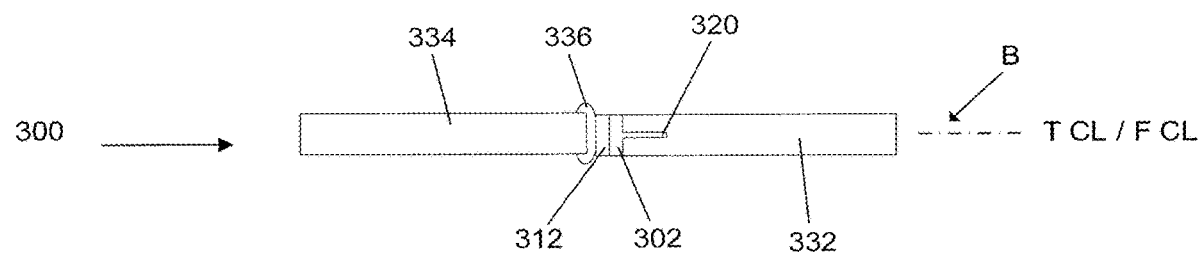
FIG. 6 is a schematic illustration of the joint and the joint balancing apparatus shown in FIG. 5 in a second configuration.

FIG. 5 is a schematic illustration of a knee balancing apparatus 300 and a knee joint in a first configuration (e.g., near maximum flexion) and FIG. 6 is a schematic illustration of knee balancing apparatus 300 with the knee joint in a second configuration (e.g., near maximum extension). Components of knee balancing apparatus 300 can be similar to, and have similar functions as, the corresponding components in knee balancing apparatus 13 200 and joint balancing apparatus 100. By way of example, a first portion 302 of knee balancing apparatus 300 can be similar in configuration to first portion 202 and first portion 102.

Knee balancing apparatus 300 includes first portion 302 including a mount 304, the first portion coupled to a tibia 332, and a second portion 312 slidably coupled to a femoral portion 336, and disposed between second portion 312 and a femur 334. Knee balancing apparatus 300 can include an intermediate portion (not shown in FIGS. 5 and 6) and a transducer (not shown in FIGS. 5 and 6) similar to that described above. Knee balancing apparatus 300 includes femoral portion 336 that is fixedly coupled to a femur 334 and is slidably coupled to second portion 312.

The knee joint includes a range of motion represented, at the beginning and end of the range of motion, by angle A and angle B, respectively. Angles A and B are the angles between a tibia centerline TCL and a femur centerline FCL. The complete range of motion of the knee joint can be, for example, from the smallest angle B or the greatest angle A to the other of the smallest angle B or greatest angle A and back. FIG. 4 depicts the knee joint in the first configuration near the greatest angle A and FIG. 5 depicts the knee joint in the second configuration near the smallest angle B. While FIG. 6 depicts the second position of the knee joint as approximately zero degrees, in some embodiments, the second position is less than zero degrees. Similarly, the greatest angle A, or flexion, of the knee joint can be greater or less than shown. As the knee joint is moved, for example, as the tibia 332 moves relative to femur 334 from the first configuration to the second configuration, the transducer outputs data, such as for example, force data, position data, displacement data, and/or rotation data to a computer system as discussed above. The transducer outputs data at predetermined intervals, such as for example, every 1 second. In other embodiments, the interval can be longer or shorter. In other embodiments, the transducer can continuously output data. The computer system can generate a signal indicative of a recommended action and output that signal for receipt and consideration by a user. In some embodiments, the signal indicative of the recommended action can be output directly to the knee balancing apparatus 300.

In some embodiments, the computer system generates a signal indicative of a recommended action prior to the knee joint finishing the range of motion. Said another way, and by way of example, a surgeon can begin with the knee joint in the first configuration at angle A, and can begin to move tibia 332 relative to femur 334 towards the second 14 configuration at angle B. In this example, the transducer can begin to output data prior to, during, or after the relative motion begins. The computer system receives the data and generates a signal indicative of a recommended action prior to the knee joint reaching the second configuration at angle B. In other embodiments, the computer system collects data associated with the movement of the tibia through its entire range of motion. In some embodiments, the computer system outputs more than one possible recommended corrective surgical procedure. In other words, the output from the computer system can be a recommendation to loosen a particular soft tissue (e.g., ligament) and/or to change the angle of a bone cut.

Figure 12:
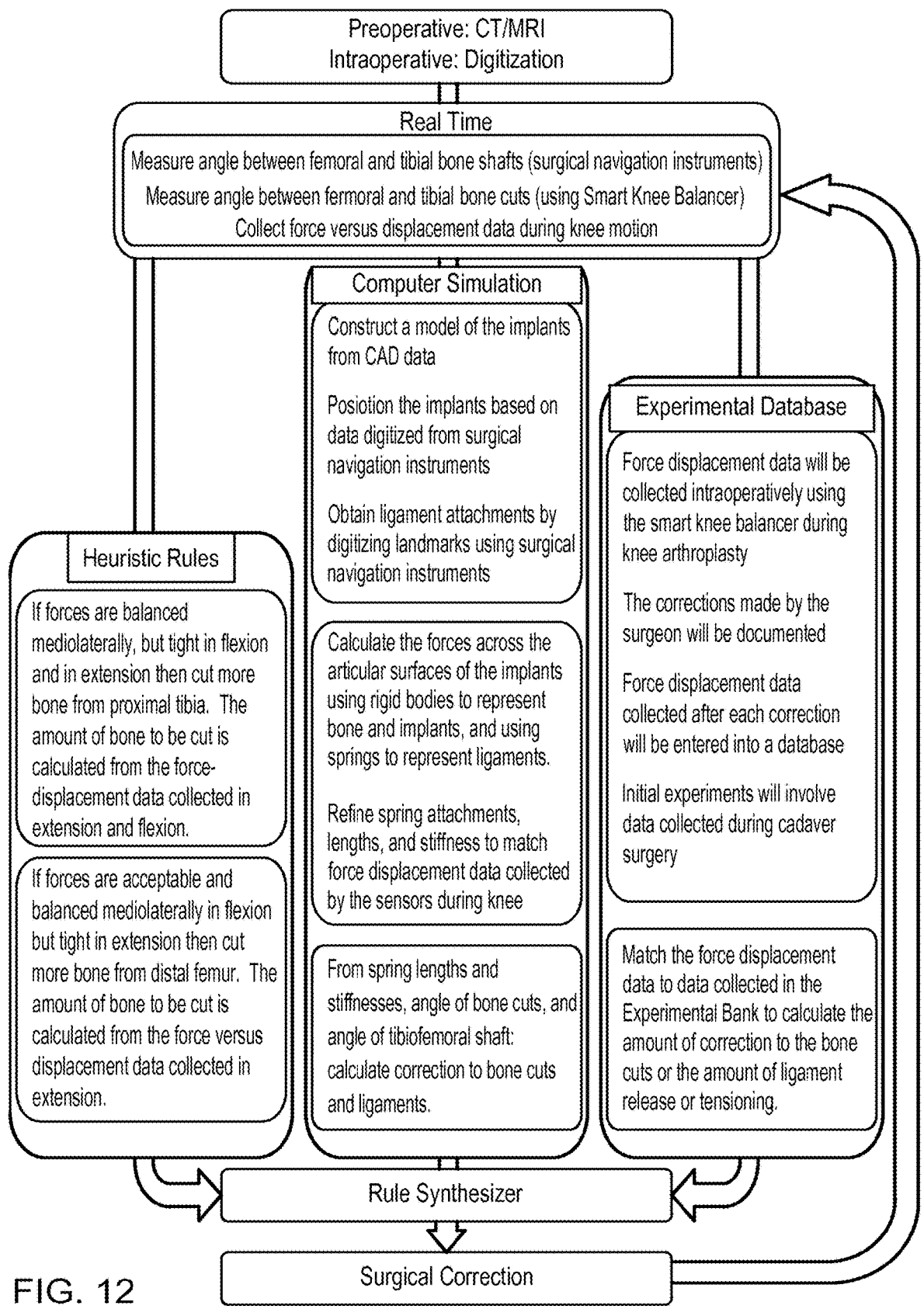
FIG. 12 is a flow chart associated with an algorithm according to an embodiment.

As discussed above, and with reference to FIG. 12, an algorithm 900 is operative to interpret the data received from the transducers in making a recommendation for a surgical procedure to correct any perceived imbalance. In some embodiments, the algorithm incorporates, for example, heuristic rules, computer simulation and an experimental data bank to accomplish its intended functionality.

Heuristic rules incorporate certain inputs acquired using the apparatus described herein, inputs from additional sources, as well as certain outputs associated with a joint balancing procedure. For example, an input includes data associated with bone geometry from, for example, a preoperative CT or MM scan, ultrasound or other imaging modality. Another input includes data associated with an angle between adjacent bony structures (e.g., the angle between femoral and tibial bone shafts) as measured using any device such as surgical instruments, computer aided navigation or robotic systems. A further input includes data associated with an angle between bone cuts (e.g., femoral and tibial bone cuts) using joint balancing apparatus (100, 200, etc.) described herein. Additional inputs include force versus displacement data in, for example, knee extension and flexion.

Outputs associated with the apparatus include, for example, surgical recommendations associated with the received inputs. For example, if various force values are received such that a determination is made that the forces are balanced mediolaterally, but tight in flexion and in extension, then a recommended output would be, for example to cut more bone from the proximal tibia (e.g., in a knee balancing situation). The amount of bone to be cut is calculated from the force versus displacement data collected in extension and flexion. If the forces are acceptable and the joint is balanced mediolaterally in flexion, but tight in extension, then a recommended output would be to cut more bone from the distal 15 femur (e.g., in a knee balancing situation). The amount of bone to be cut is calculated from the force versus displacement data collected in extension.

The algorithm includes/relies on computer simulation of a procedure associated with real time events (i.e., during a surgical procedure) and/or a database of simulated procedures. During a surgical procedure, for example, inputs are received similar to the manner described above. For example, relevant bone geometry is obtained from a preoperative CT scan. Additional data associated with bone geometry can be obtained from readings/measurements from devices such as surgical instruments, computer aided navigation, or robotic systems. A model of the implants to be used in the surgical procedure area constructed using computer aided design (CAD) data. The simulated/model implants are positioned based on the digitized data obtained from the surgical navigation instruments. Ligament attachment locations for the simulation are obtained by digitizing landmarks using surgical navigation instruments or from preoperative or intraoperative imaging. Force versus displacement data is collected for the joint (e.g., a knee joint) during flexion and extension.

The computer simulation relies on computer models created using various techniques. For example, a model of the forces across the articular surfaces of the implants can be derived from calculations utilizing rigid bodies to represent bone and implants and using springs to represent ligaments. The spring attachments, lengths, and stiffness values can be refined to match force displacement data collected by the sensors/transducers during joint flexion and extension. From the spring lengths and stiffnesses, angle of bone cuts, and angle of the tibiofemoral shaft, corrections to bone cuts and ligaments can be calculated.

In some embodiments, a simulation database or databank can be generated. The database (or atlas) can include a variety of femur bones and tibia bones. For example the database can include bones of varying sizes (e.g., very small, small, medium, large, very large) and can be associated with a variety of factors such as, for example, demographic factors (e.g., gender, race, bone structure, etc.). A model of the relevant associated implants can be constructed from CAD data as discussed above. Combinations of implant position, implant rotation and ligament tightness can be created for reference.

A computer model is created and a model of the forces across the articular surfaces of the implants can be derived from calculations utilizing rigid bodies to represent bone and implants and using springs to represent ligaments. During a surgical procedure, the 16 force data, etc. that is collected is compared with data from the simulation database. The implant position, rotation and ligament tightness condition from the database that most closely matches the intraoperative data is identified. In some embodiments, the identification is manual. In other embodiments, the identification is automatic.

The implant position, rotation, and ligament tightness conditions are utilized to calculate the amount of correction to the bone cuts or the amount of ligament release or tensioning that is required. Based on the calculations, a recommendation is provided to make the appropriate correction when necessary.

In some embodiments, the algorithm includes an experimental database. The database includes data such as, for example, force displacement data collected intraoperatively using the joint balancing device as discussed herein. For example, the data can include force data from a knee balancing device collected intraoperatively during a knee arthroplasty. Any corrections made intraoperatively would be documented. Force displacement data collected after each correction is collected/entered into a database to supplement or replace the simulation database discussed above. In some embodiments, the data is collected during cadaver-based surgical procedures.

The force displacement data collected during a subsequent procedure is compared to data collected in the experimental database. Based on the calculations, a recommendation is provided to make the appropriate correction (e.g., amount of correction to bone cuts and/or amount of ligament release or tensioning) when necessary.

Figure 7:
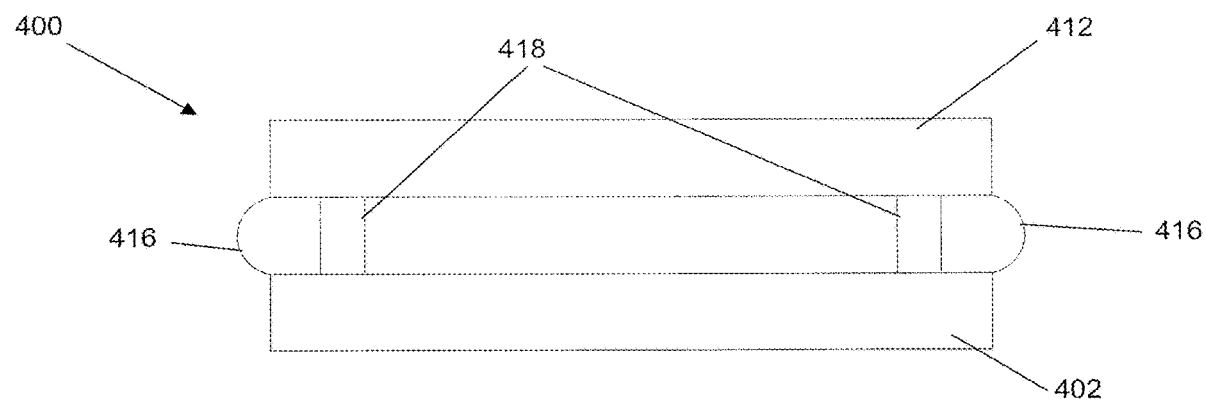
FIG. 7 is a schematic illustration of a joint balancing apparatus according to an embodiment.
Figure 8:
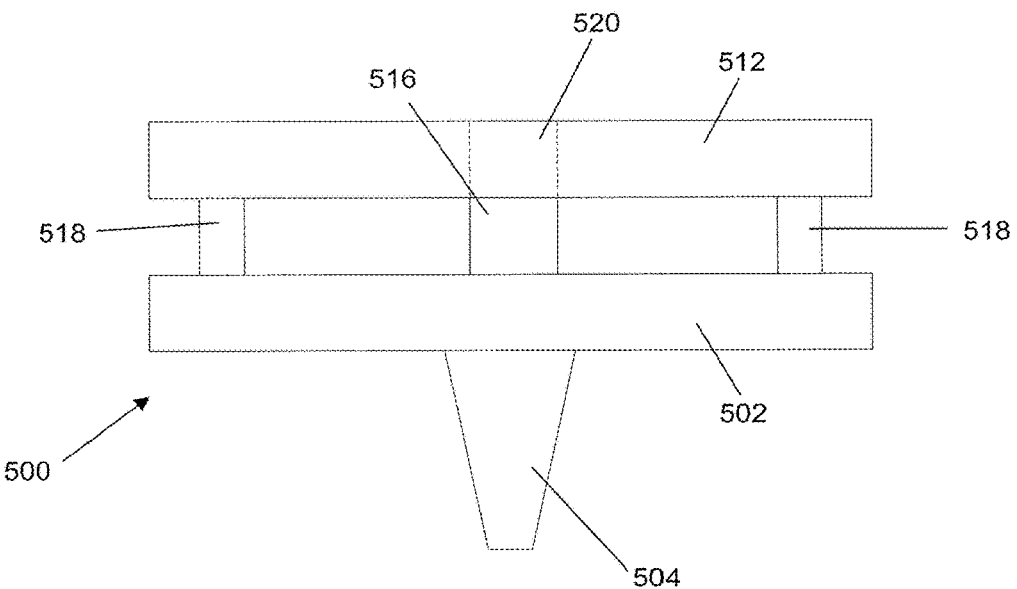
FIG. 8 is a schematic illustration of a joint balancing apparatus according to an embodiment.

FIG. 7 is a front view of a joint balancing apparatus 400 according to an embodiment, and FIG. 8 is a front view of a joint balancing apparatus 500 according to an embodiment. Joint balancing apparatus 400 and joint balancing apparatus 500 can be similar to joint balancing apparatus 100, knee balancing apparatus 200 and knee balancing apparatus 300. In this manner, components of joint balancing apparatus 400 and joint balancing apparatus 500 can be similar to and have similar functions as the corresponding components in knee balancing apparatus 300, knee balancing apparatus 200, and joint balancing apparatus 100. By way of example, a first portion 402 of knee balancing apparatus 400 and a first portion 502 of knee balancing apparatus 500 can be similar in configuration to first portion 202 and first portion 102. While a front view is illustrated in FIG. 7, it should be understood that sensors/transducers associated with movement of the knee-balancing device in 6 degrees 17 of freedom is contemplated. In other words, the transducers can also detect anterior/posterior movement, medial/lateral movement, translation and rotation.

Joint balancing apparatus 400 includes first portion 402, a second portion 412, an intermediate portion 416, and two transducers 418. While depicted in FIG. 7 as including two transducers 408, in some embodiments, joint balancing apparatus 400 can include more or fewer transducers 408. In contrast to intermediate portion 216 of knee balancing apparatus 200, intermediate portion 416 extends around the perimeter of the apparatus 400. Intermediate portion 416 can be fixedly coupled to first portion 402 and second portion 412. In some embodiments, intermediate portion 416 can extend around first portion 402 and second portion 412, and, in this manner, can define a fully enclosed volume between first portion 402 and second portion 412. In other embodiments, intermediate portion 416 can extend around only a portion of first portion 402 and second portion 412, and, in this manner, can define a partially enclosed volume between first portion 402 and second portion 412. In still other embodiments, intermediate portion 416 can include a plurality of intermediate portions 416 each of which extend around a portion of first portion 402 and second portion 412 to combine to either fully or partially define a volume between first portion 402 and second portion 412. Depending on the portion of the apparatus 400 around which the intermediate portion 416 extends, the relative movement of the first portion 402 and the second portion 412 can be defined. Additionally, depending on the material properties (e.g., elasticity) of the intermediate portion 416, the relative motion of the first portion 402 and second portion 412 can be dictated. As shown in FIG. 7, transducers 408 are disposed within the volume between first portion 402 and second portion 412. While shown as including only transducers 408, joint balancing apparatus 500 can also include actuators as described herein.

Joint balancing apparatus 500 includes first portion 502, a second portion 512, an intermediate portion 516, and two transducers 508. While depicted in FIG. 8 as including two transducers 508, in some embodiments, joint balancing apparatus 500 can include more or fewer transducers 508. As shown in FIG. 8, first portion 502 includes a mount 504 configured to be disposed in a cavity within a first bony structure, and intermediate portion 516 is substantially linear in configuration and is configured to be at least partially disposed within an aperture 520 of second portion 512. While shown as including only transducers 508, joint balancing apparatus 500 can also include actuators as described herein.

Figure 9:
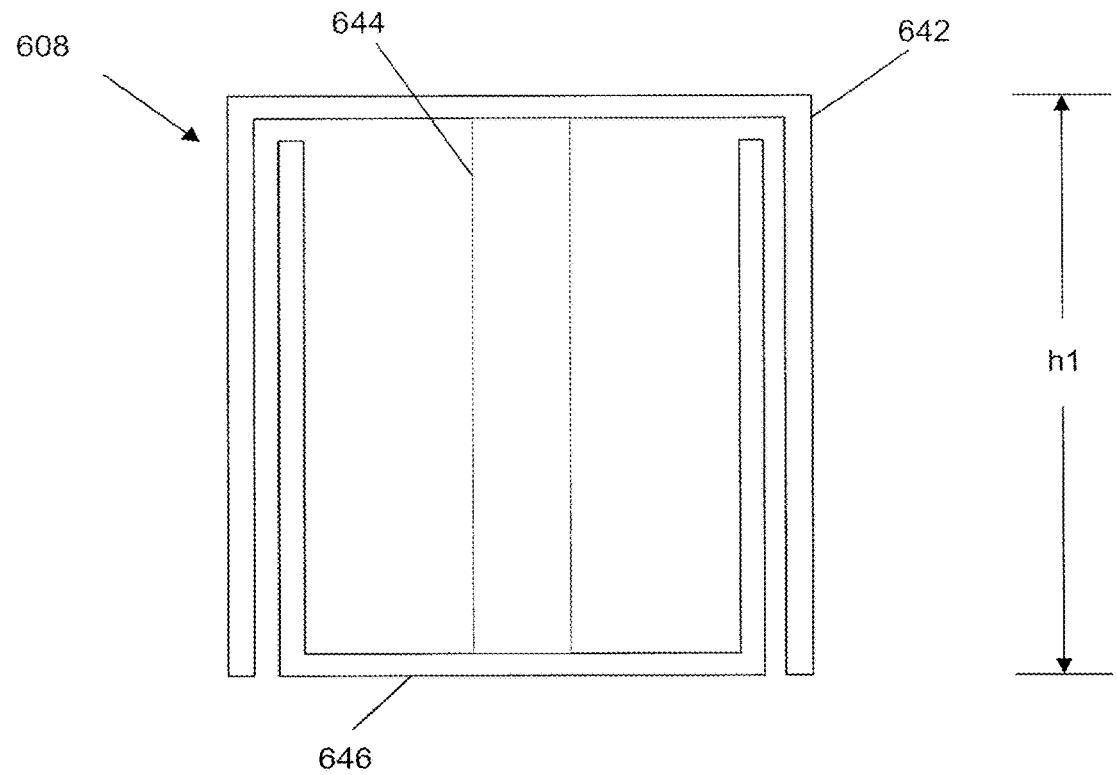
FIG. 9 is a cross-sectional schematic illustration of a transducer/actuator of a joint balancing apparatus according to an embodiment in a first configuration.

FIG. 9 is a front cross-sectional view of an example of a transducer 608 in a first configuration, and FIG. 9 is a front cross-sectional view of transducer 608 in a second configuration. Transducer/actuator 608 can be similar to any of transducers 108, 208, 308, 408, or 508. In this manner, components of transducer/actuator 608 can be similar to and have similar functions as the corresponding components in any of transducers 108, 208, 308, 408, or 508. By way of example, a fixed portion 646 of transducer/actuator 608 can be similar in configuration to the fixed portion of transducer 108. Transducer/actuator 608 can include fixed portion 646, a movable portion 642, and an actuation and electronics assembly ("actuation assembly") 644.

Figure 10:
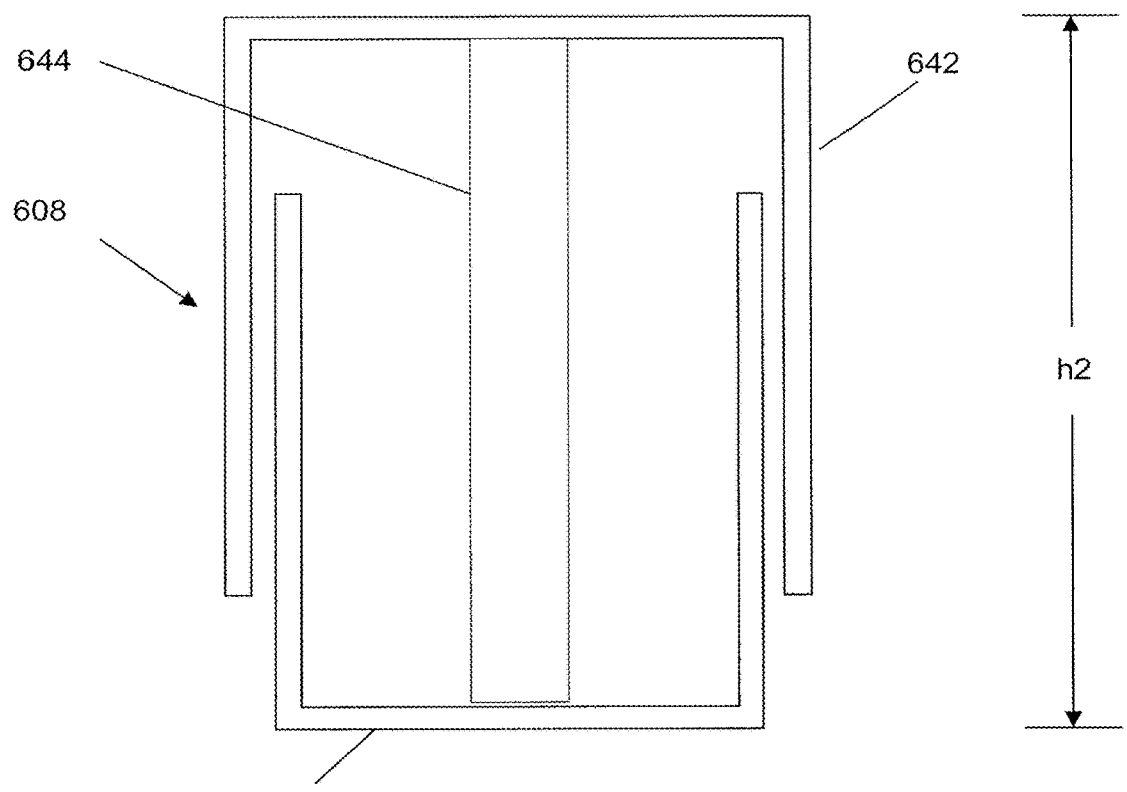
FIG. 10 is a cross-sectional schematic illustration of the transducer/actuator shown in FIG. 9 in a second configuration.

Fixed portion 646 is configured to be coupled to one of a first portion (not shown) or a second portion (not shown in FIGS. 9 and 10) of a joint balancing apparatus (not shown in FIGS. 9 and 10). Fixed portion 646 can be coupled permanently or temporarily to the first portion or the second portion and can be fixed mechanically, magnetically, and/or chemically. In this manner, when the first portion moves relative to the second portion, the location of transducer 608/actuator relative to first or the second portion can be maintained.

Movable portion 642 is configured to be coupled to the other of the first portion or the second portion of the joint balancing apparatus, and is operatively coupled to the fixed portion via the actuation assembly 644. Movable portion 642 can be slidably coupled to the first portion or the second portion. In this manner, when the first portion moves relative to the second portion the transducer/actuator 608 can freely slide about the portion to which movable portion 642 is coupled.

Actuation assembly 644 can include an actuation mechanism (not shown in FIGS. 9 and 10) configured to move fixed portion 646 relative to movable portion 642 in response to a received signal, or plurality of signals. A signal can include a signal indicative of a recommended action or to simulate that recommended action. The actuation mechanism can be inflatable, piston-based, spring-based, and/or motor based, and can be hydraulic, pneumatic, electric, magnetic, thermal, piezoelectric and/or manual. Actuation assembly 644 is configured to output data, such as for example, force data, position data, displacement data, and/or rotation data relating to the interaction of the first portion relative to the second portion. The electronics mechanism can be configured to output data to a computer system (not shown in FIGS. 9 and 10), and to receive signals from the computer system. The electronics mechanism can output data wirelessly or via wire. The electronics mechanism 19 can be configured to manipulate the actuation mechanism in response to the received signals. In some embodiments, actuation assembly 644 can be configured to receive signals indicative of recommended action and/or simulated recommended action.

By way of a example, transducer/actuator 608 can be in a first configuration. When in the first configuration, fixed portion 646 can be fixedly coupled to a first portion of a joint balancing apparatus, and movable portion 642 can be slidably coupled to a second portion of the joint balancing apparatus. The distance between a distal surface of the second portion and a proximal surface of the first portion can be height h1. Transducer/actuator 608 can receive a signal indicative of a recommended action and, in order to simulate the results of the recommended action, the actuation mechanism moves movable portion 642 relative to fixed portion 646 until the distance between the distal surface of the second portion and the proximal surface of the first portion, at the position of transducer 608, can be height h2.

In another example, when in the first configuration, fixed portion 646 can be fixedly coupled to a first portion of a joint balancing apparatus, but movable portion 642 may not be slidably coupled to a second portion of the joint balancing apparatus. The distance between a distal surface of the second portion and a proximal surface of the first portion is unknown. The actuation mechanism moves movable portion 642 relative to fixed portion 646 until fixed portion 646 is slidably coupled to the second portion. In some embodiments, the actuation assembly can cause the actuation mechanism to move movable portion 642 relative to fixed portion 646 until fixed portion 646 is slidably coupled to the second portion and continue to actuate movable portion 642 until a force between the first portion and the second portion is substantially at a predetermined value, or within a predetermined range. In such embodiments, the predetermined value can be an expected range of a stable joint.

In some embodiments, each of a plurality of transducers/actuators 608 can be actuated such that the output data of each of the transducers indicates substantially the same force between the first portion and the second portion, and the output data also indicates the height of each of the transducers 608 at the predetermined force. The output data is analyzed and/or interpreted via an algorithm and can result in a recommended action that may result in a change in height of one or more of transducers/actuators 608. By way of example, a first transducer/actuator may be actuated until the force between a first portion and a second portion at the location of the first transducer is X, and, at force X the first transducer/actuator height can be h1. A second transducer/actuator may be actuated until the force between a 20 first portion and a second portion at the location of the second transducer/actuator is X, and, at force X the second transducer/actuator height can be h2. Each of the first transducer/actuator and the second transducer/actuator can output force and height data to a computer system, and the computer system can generate a signal indicative of a recommended action based on that data. The first transducer/actuator and the second transducer/actuator can receive the signal from the computer system and can be actuated to simulate a surgical procedure to simulate the results of the recommended action. In some embodiments, the simulated procedure can include manipulating other transducers/actuators to increase or decrease the height of the first transducer/actuator and/or second transducer/actuator while maintaining the force between the first portion and second portion. In some embodiments, known forces are applied to simulate various conditions and monitor the behavior/performance of the apparatus under those conditions (i.e., standing, walking, running, jumping, etc.).

In some embodiments (not illustrated) the transducers/actuator are replaced by a sheet or layer of piezoelectric material configured to perform in substantially the same manner as described with respect to the transducers/actuators. The piezoelectric material may cover all or just a portion or certain portions of the second portion of the balancing apparatus. In some embodiments, the piezoelectric material is configured such that a movable second portion is not required, but rather the piezoelectric material is sufficiently flexible enough to be displaced a sufficient amount.

In some embodiments, each of a plurality of transducers/actuators 608 can be actuated such that the output data of each of the transducers indicates substantially the same distance between the first portion and the second portion, and the output data also indicates the force data of each of the transducers/actuators 608. The computer system can analyze the output data and can recommend an action that may result in a change in force between the first portion and the second portion at the location of one or more of transducers/actuators 608. By way of example, a first transducer/actuator may be actuated until the distance between a first portion and a second portion at the location of the first transducer/actuator is h2 (or some other height), and the force between the first portion and the second portion at the location of the first transducer/actuator can be X. A second transducer/actuator may be actuated until the distance between a first portion and a second portion at the location of the second transducer is h2, and the force between the first portion and the second portion at the 21 location of the second transducer/actuator can be Y. Each of the first transducer/actuator and the second transducer/actuator can output force and height data to a computer system, and the computer system can generate a signal indicative of a recommended action. As the corrective action is taken by the surgeon, data is output by the transducers/actuators to determine if the corrective action was effective and appropriate real-time updates are provided.

Figure 11:
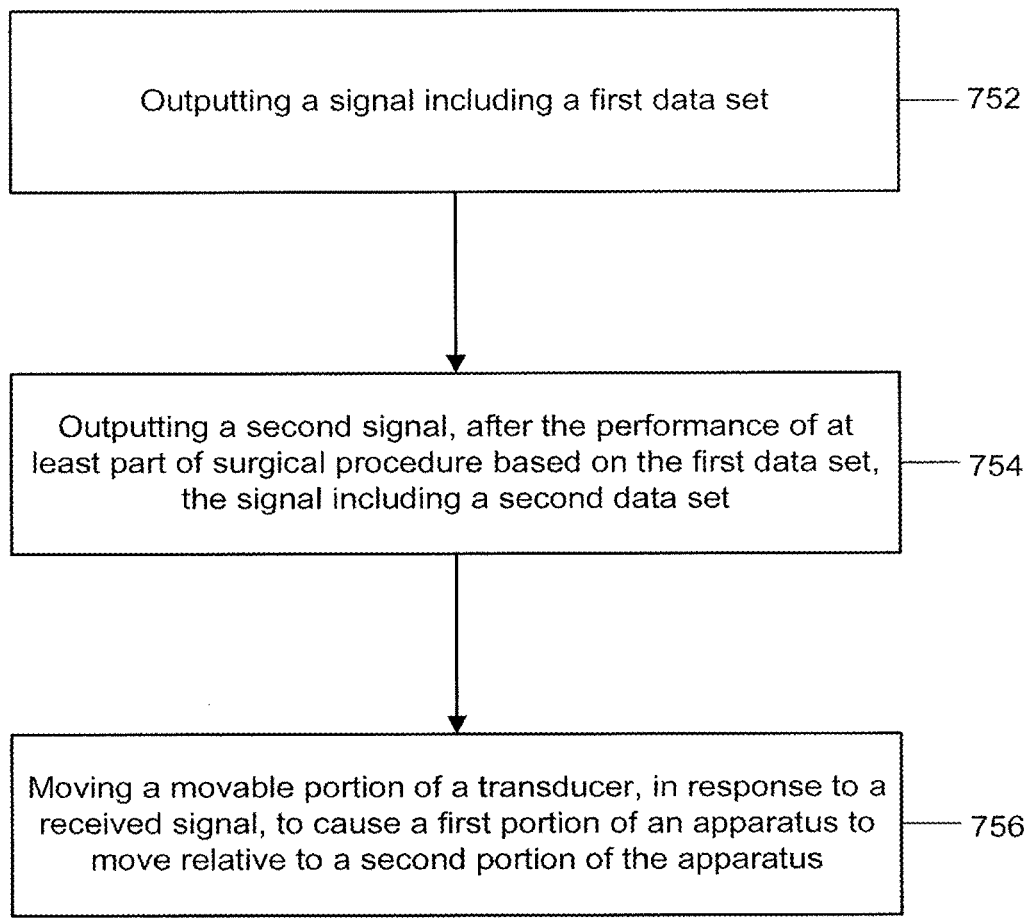
FIG. 11 is a flow chart of a method of balancing a joint using a joint balancing apparatus according to an embodiment.

FIG. 11 is a flow chart depicting a method 750 for balancing a joint using a joint balancing apparatus disclosed herein. Method 7 50 includes outputting a signal including a first data set, 752. The first data set can be associated with at least one of a force, a position, a displacement or a rotation associated with a joint balancing apparatus disposed between first a bony structure of the joint and a second bony structure of the joint. Method 750 includes outputting a second signal, after the performance of at least part of a surgical procedure based on the first data set, 754. The second signal includes a second data set that can be associated with at least one of a force, a position, a displacement or a rotation associated with the joint balancing apparatus after the performance of at least part of the surgical procedure. Method 750 includes moving a movable portion of an actuator, in response to a received signal, to cause a first portion of an apparatus to move relative to a second portion of the apparatus, 756.

By way of example, and with reference to FIG. 3 and FIG. 4, a method includes using knee balancing apparatus 200 to balance a knee joint. The method can include one or more of transducers 208 outputting a signal including a first data set. The first data set can include, for example, the force between first portion 202 and second portion 212 at each transducer location. More specifically, transducer 208A and transducer 208B can each output a signal indicating a force of X, and transducer 208C and transducer 208D can each output a signal indicating a force of Y, force Y being lower than force X. In some embodiments, each of the forces output by the transducers is different. In some embodiments, transducers 208 can output the signal while the knee joint is moving from a first position of a range of motion to a second position of a range of motion. In some embodiments, transducers 208 can output a plurality of signals while the knee joint is moving from a first position of a range of motion to a second position of a range of motion. The signal including the first data set can be received by a computer system, and the computer system can generate a signal indicative of a recommended action, for example, a surgical procedure to lower force X and/or raise force Y. 22 In some embodiments, the recommended action can include modifying one or more connective tissues and/or making one or more bone cuts.

In some embodiments, each of transducers/actuators 208 can receive the signal from the computer system, and can move each of the movable portions relative to each of the fixed portions, as needed, to simulate the recommended action. The method can include one or more of transducers 208 outputting a second signal including a second data set. The second data set can include, for example, the force between first portion 202 and second portion 212 at each transducer location, after moving the movable portions of the transducers 208 relative to the fixed portions of the transducers/actuators 208. More specifically, transducer/actuator 208A and transducer/actuator 208B can each output a signal indicating a force of X, and transducer/actuator 208C and transducer/actuator 208D can each output a signal indicating a force of Y, force Y being substantially the same as force X. In some embodiments, transducers/actuators 208 can output the second signal while the knee joint is moving from a first position of a range of motion to a second position of a range of motion. In some embodiments, transducers/actuators 208 can output a plurality of second signals while the knee joint is moving from a first position of a range of motion to a second position of a range of motion. In this example, because the force X and the force Y are substantially the same, the surgeon can complete the recommended action.

Once the surgeon is satisfied that the knee is appropriately balanced (i.e., the soft tissue as well as the hard tissue), the apparatus 200 (similarly 100, 300, 400, 500, etc.) can be removed from the body. The surgeon can subsequently place a more permanent or final implant in its place. The dimensions and physical characteristics of the final implant are substantially the same as the balancing apparatus. Thus, when the final implant is in position, the knee remains properly balanced.

While various embodiments have been described above, it should be understood that they have been presented by way of example only, and not limitation. Where methods described above indicate certain events occurring in certain order, the ordering of certain events can be modified. Additionally, certain of the events can be performed concurrently in a parallel process when possible, as well as performed sequentially as described above. Although various embodiments have been described as having particular features and/or combinations of components, other embodiments are possible having a combination of any features and/or components from any of embodiments where appropriate. By way of 23 example, the examples and embodiments described with reference to transducer 608 can be applicable to the other transducers described and to the associated joint balancing apparatus.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor readable medium) is non-transitory in the sense that it does not include transitory propagating signals per se (e.g., a propagating electromagnetic wave carrying information on a transmission medium such as space or a cable). The media and computer code (also can be referred to as code) can be those designed and constructed for the specific purpose or purposes. Examples of computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CDROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or microinstructions, machine instructions, such as produced by a compiler, code used to produce a web service, and files containing higher-level instructions that are executed by a computer using an interpreter. For example, embodiments can be implemented using Java, C++, or other programming languages (e.g., object-oriented programming languages) and development tools. Additional examples of computer code include, but are not limited to, control signals, encrypted code, and compressed code.

While various embodiments have been described above, it should be understood that they have been presented by way of example only, not limitation, and various changes in form and details can be made. By way of example, while knee balancing apparatus 200 is described as having a post-shaped intermediate portion 216, in some embodiments, knee balancing apparatus 200 can include an intermediate portion, similar to intermediate portion 416 shown in FIG. 5. Any portion of the apparatus and/or methods described herein can be combined in any combination, except mutually exclusive combinations. The embodiments 24 described herein can include various combinations and/or sub-combinations of the functions, components and/or features of the different embodiments described.

In some embodiments, the balancing apparatus does not include an intermediate portion. In such an embodiment, the transducers themselves act to limit/define the relative movement of the second portion of the apparatus with respect to the first portion of the apparatus.

What is claimed is:

1. In a joint replacement balancing system which provides real-time feedback to a surgeon during a joint replacement surgery to assist the surgeon to balance a joint replacement, a non-transitory processor-readable medium storing code representing instructions to cause a processor to:
   receive a signal, wherein the signal communicates a first data set including a joint balancing parameter,
      wherein the joint balancing parameter is determined based at least in part on displacement of a joint caused by a joint balancing apparatus disposed between a first bony structure and a second bony structure,
      wherein the joint balancing apparatus comprises
         a first portion configured to be coupled to the first bony structure,
         a second portion configured to be disposed between the first portion and the second bony structure, and
         an actuator disposed between the first portion and the second portion and configured to move the first portion relative to the second portion;
   determine, based on the first data set, if the joint replacement is out of balance;
   determine, based on the first data set, a corrective course of action to bring the joint into balance; and
   generate and display to the surgeon during the joint replacement surgery the corrective course of action to complete the joint replacement surgery.

2. The non-transitory processor-readable medium of claim 1, wherein the joint balancing parameter comprises at least one of a force, a position, a displacement or a rotation associated with the joint balancing apparatus.

3. The non-transitory processor-readable medium of claim 1, wherein the display of the recommended action comprises displaying a recommendation selected from the group consisting of selecting an appropriate prosthesis, removing bone, tensioning ligament or removing ligament.

4. The non-transitory processor-readable medium of claim 1, wherein the code representing instructions to cause a processor to receive the signal includes code to receive the signal as the joint balancing apparatus is moved through a predefined range of motion during the surgery.

5. The non-transitory processor-readable medium of claim 1, wherein the code representing instructions to cause a processor to receive the signal includes code to receive a plurality of signals as the first bony structure is moved through a predefined range of motion with respect second bony structure during the surgery.

6. The non-transitory processor-readable medium of claim 1, further including code representing instructions to cause a processor to receive a signal including a second data set, the second data set associated with at least one of a force, a position, a displacement or a rotation associated with the apparatus after the performance of at least a part of a surgical procedure.

7. The non-transitory processor-readable medium of claim 1, wherein the instructions cause the processor to provide the corrective course of action by displaying a chart illustrating the corrective course of action.

8. The non-transitory processor-readable medium of claim 1, wherein the instructions cause the processor to provide the corrective course of action by displaying an animation illustrating the corrective course of action.

9. The non-transitory processor-readable medium of claim 1, wherein the instructions cause the processor to provide the corrective course of action by displaying a graphical figure illustrating the corrective course of action.

10. The non-transitory processor-readable medium of claim 1, wherein the instructions cause the processor to provide the corrective course of action by outputting an auditory message providing the corrective course of action.

11. The non-transitory processor-readable medium of claim 1, wherein the instructions cause the processor to provide the corrective course of action by outputting tactile feedback providing the corrective course of action.

12. The non-transitory processor-readable medium of claim 1, further including code representing instructions to cause a processor to repeat the steps of (a) receiving the signal, (b) determining if the joint replacement is out of balance, (c) determining the corrective course of action, and (d) generating and displaying the corrective course of action.

13. The non-transitory processor-readable medium of claim 1, wherein the determination of the corrective course of action for the joint replacement surgery is based on a computer simulation of a procedure associated with real time events during the surgical procedure.

\* \* \* \* \*